United States Patent
Katinger et al.

[11] Patent Number: 5,911,989
[45] Date of Patent: Jun. 15, 1999

[54] HIV-VACCINES

[75] Inventors: Hermann Katinger; Andrea Buchacher; Wolfgang Ernst; Claudia Ballaun; Martin Purtscher; Alexandra Trkola, all of Vienna; Renate Predl, Deutsch-Wagram; Christine Schmatz, Vienna; Annelies Klima, Vienna; Franz Steindl, Vienna; Thomas Muster, Vienna, all of Austria

[73] Assignee: Polynum Scientific Immunbiologische Forschung GmbH, Vienna, Austria

[21] Appl. No.: 08/478,536

[22] Filed: Jun. 7, 1995

Related U.S. Application Data

[63] Continuation-in-part of application No. PCT/EP95/01481, Apr. 19, 1995.

[51] Int. Cl.$^6$ .......................... A61K 39/42; A61K 39/21; C12Q 1/70; C07K 16/00
[52] U.S. Cl. .................................. 424/160.1; 530/388.35; 424/208.1; 435/5
[58] Field of Search ........................ 424/160.1, 208.1; 530/388.35; 435/5

[56] References Cited

U.S. PATENT DOCUMENTS

| | | | |
|---|---|---|---|
| 4,761,470 | 8/1988 | Emini et al. | 530/326 |
| 5,087,557 | 2/1992 | McClure | 435/5 |
| 5,245,015 | 9/1993 | Fung et al. | 530/388.35 |
| 5,516,657 | 5/1996 | Murphy et al. | 435/69.3 |

OTHER PUBLICATIONS

Fahey et al., Status of immune–based therapies in HIV infection and Aids Clin. Exp. Immunol. (1992)88, 1–5, Jan. 1992.

Luckow et al., Trends in the development of Baculovirus expression vectors, Bio/Tech vol. 6, pp. 47–55, see Abstract and p. 47, column 1, sentence 4, Jan. 1988.

Ratner et al., Complete nucleotide sequence of the AIDS virus, HTLV–III, Nature 313:277–284, Jan. 1985.

Primary Examiner—Jeffrey Stucker
Assistant Examiner—Hankyel T. Park
Attorney, Agent, or Firm—Birch, Stewart, Kolasch & Birch, LLP

[57] ABSTRACT

Disclosed are antibodies which can be used for the manufacture of vaccines for active and/or passive immunization of persons in need of such treatment. The invention also provides for human monoclonal antibodies that are functionally equivalent to the above-mentioned antibodies produced by any one of the cell lines CL1 through CL6 (deposited at the European Collection of Animal Cell Cultures (ECACC) at the PHLS in Porton Down, Salisbury, UK). Also provided are hybridoma and/or CHO cell lines producing any one of the antibodies disclosed and claimed herein. Also provided are mixtures of antibodies of the present invention, as well as methods of using individual antibodies or mixtures thereof for the detection, prevention and/or therapeutical treatment of HIV-1 infections in vitro and in vivo.

20 Claims, 6 Drawing Sheets

HIV-VACCINES

This application is a continuation-in-part of PCT international application No. PCT/EP95/01481 which has an international filing date of Apr. 19, 1995 which designated the United States, the entire contents of which are hereby incorporated by reference.

BACKGROUND OF THE INVENTION

1. Technical Field

The present invention is in the field of immunology, especially detection, prevention and treatment of HIV-1 infection and AIDS therapy. More particularly, it concerns monoclonal antibodies, drugs and vaccines made from these antibodies and methods based on the use of these antibodies, drugs and vaccines for analytical and/or clinical applications.

2. Description of Related Art

In the sera of human immunodeficiency virus type 1 (HIV-1) infected patients, anti-virus antibodies can be detected over a certain period after infection without any clinical manifestations of the acquired immunodeficiency syndrome (AIDS). At this state of active immune response, high numbers of antigen-specific B-cells are expected in the circulation. These B-cells are used as fusion partners for the generation of human monoclonal anti-HIV antibodies.

Monoclonal antibodies can be produced by known procedures, e.g., as described by R. Kennet et al. in "Monoclonal Antibodies and Functional Cell Lines; Progress and Applications". Plenum Press (New York), 1984.

Further materials and methods applied are based on known procedures, e.g., such as described in J. Virol. 67:6642–6647, 1993.

Monoclonal antibodies and in particular human monoclonal antibodies have been widely used in the last few years in order to improve the understanding of HIV-1 neutralization by antibodies released upon immunization with HIV-1 derived immunogens or upon infection in afflicted patients (J. Virol. 62:2107–2114, 1988; Immunology 76:515–534, 1992; J. Virol. 67:6642–6647, 1993; U.S. Pat. No. 5,087,557). Many efforts have been made to overcome the detrimental capability of the HIV-1 virus to rapidly change its morphology under immunological pressure and thereby to escape the capture by antibodies released from a patient's immune system or developed and applied by researchers. As a result thereof, there is presently no reliable antibody-based (nor any other) vaccine for active or passive immunization on the market.

One significant step forward has been made when an antigenic determinant on the smaller subunit gp41 of the HIV-1 envelope glycoprotein gp160 was found (EP 570 357 A2), which corresponds to the amino acid sequence "ELDKWA" located at amino acid position number 662 to 667 of gp41 of HIV-1 isolate BH10. The authors report therein an HIV-1 neutralizing human monoclonal antibody specifically binding to said antigenic determinant. The antibody proved to be a powerful tool for biochemical analysis of the binding epitope and its variability. The discovery of the highly conserved state of said gp41-epitope gave rise to the hope of possibly finding a vaccine composition suitable for more reliable prevention of human individuals from HIV-1 infection and/or for more successful therapeutic treatment of infected patients.

The results reported in EP 570 357 A2 motivated the present inventors to intensify their research activities which finally led them to the novel and inventive findings herein disclosed.

However, in spite of promising results of the art relating to the use of HIV-1 neutralizing monoclonal antibodies, there is at least one major drawback to this sort of approach. It lies in the wide-spread use of laboratory strains of HIV-1 isolates, which have become adapted to lab-conditions and are more or less attenuated and hence only poorly—if at all—representative of the properties and behaviour of primary HIV-1 isolates. Consequently, promising vaccine compositions drawn against laboratory HIV-1 strains frequently proved non-efficacious when applied against primary HIV-1 isolates, e.g., of blood samples of infected persons (see J. Cohen, Science 262:980–981, 1993).

The second major drawback was and still is the ability of the HIV-1 virus to escape antibody capture by morphological variation, which very often renders the remarkable efforts of the researchers almost useless. Such escape mutants may be characterized by a change of only one or several of the amino acids within one of the targeted antigenic determinants and may occur, e.g., as a result of spontaneous or induced mutation.

SUMMARY OF THE INVENTION

The present invention therefore provides antibodies which have been found to overcome the disadvantages of the prior art and which can be used for the manufacture of vaccines for active and/or passive immunization of persons in need of such treatment. Such beneficial antibodies are, for instance, produced by any one of the cell lines CL1 through CL6 listed below. The Invention also provides for human monoclonal antibodies that are functionally equivalent to the antibodies of CL1 through CL6. These functionally equivalent antibodies substantially share at least one major functional property with an antibody of CL1 to CL6 as herein described, comprising: binding specificity to gp160; binding dependence on glycosylation; reactivity in the presence of tunicamycin; inhibition of infections of human lymphocytes by primary HIV-1 isolates; reactivity towards antiidiotypes; competition for same binding site; reduction of the HIV-1 level in blood serum after intravenous administration to an infected patient; and/or specific binding to HIV-1 neutralizing antibodies.

It is also an object of the present invention to provide for the hybridoma and/or CHO cell lines producing any one of the antibodies disclosed and claimed herein.

The invention is further directed to mixtures of antibodies according to the present invention, as well as to methods of using individual antibodies or mixtures thereof for the prevention and/or therapeutical treatment of HIV-1 infections in vitro and in vivo, and/or for improved detection of HIV-1 infections.

The cell lines CL1 to CL4 produce monoclonal antibodies recognizing HIV-envelope glycoproteins, and in particular specific antigenic determinants of gp160. The antibodies of CL1 and CL4 recognize and bind to an amino acid sequence of gp41/gp160 corresponding to the epitope located at amino acid position number 662 to 667 ("ELDKWA") of gp41 of HIV-1 isolate BH10 (GenBank accession M15654; numbering as described in the Swissprot database entry ENV$HIV10). The monoclonal antibodies of CL2 and CL3 bind to two different antigenic determinants, more particularly to fragments of gp120/gp160 corresponding to the epitope sequences located at amino acid positions 79 to 184 and 326 to 400 respectively, of processed gp120 of HIV-1 isolate BH10 (GenBenk accession M15654; numbering as described in the Swissprot database entry ENV$HIV10).

While the idiotypic antibodies produced by CL1 to CL4 are directed to the capture and neutralization of HIV-1 viruses in vitro and in vivo, the antiidiotypic antibodies released from CL5 and CL6 take an opposite role, i.e., they mimic the viruses, more particularly they mimic the corresponding antigenic determinant(s) of the HIV-1 viruses. The anti-idiotypic antibodies of CL5 and CL6 are of a nature such that they bind to the idiotypic antibody of CL2 at essentially the same location(s) (antigenic determinants) on gp160 as does the virus itself.

BRIEF DESCRIPTION OF THE DRAWINGS

FIG. 2A shows the failure of a CL2 antibody to bind to the deglycosylated form (lane 3) of gp160 of HIV-1, while MAb CL1 (FIG. 2B) was used as a control because it successfully binds to the deglycosylated gp160;

FIG. 4A shows the blocking effect of antibodies M1G1 through 4C12 toward HIV-1 neutralizing monoclonal antibodies of the CL2 (plot A) and CL1 (FIG. 4B) cell line in a p24 antigen ELISA; the anti-idiotypic character of M1G1 towards MAb CL2 is demonstrated;

FIG. 5 shows the uniqueness of antibodies of the CL2 and the CL3 (=recomb. CL2) cell lines among a multitude of different anti-HIV antibodies; only the antibodies of CL2 and CL3 are recognized and bound by the anti-idiotypic antibodies M1G1 (plot A) and M1A3 (FIG. 5B);

FIG. 6 shows HIV-1 neutralizing efficacy of antibodies of call line CL1 after in vivo application to a human patient: triangles show the HIV-induced formation of syncytia in the serum taken from an infected patient before administration of CL1 antibodies, while squares demonstrate complete failure of syncytia formation after administration of CL1 antibodies.

DETAILED DESCRIPTION OF THE INVENTION

The contents of each of the references cited herein are herein incorporated by reference in their entirety.

When conducting experiments to find novel anti-HIV-1 antibodies the inventors found human monoclonal antibodies which could be shown to efficiently neutralize HIV-1 in vitro including a variety of primary HIV-1 isolates, such as, e.g., primary HIV-1 isolates 92RW009, 82RW021, 92UG037, 92TH014. 92BR030, N70-2, DJ259 (all obtained from WHO network for HIV-1 isolation and characterization), or WYG, WRF, WRB, WSC. WHM (isolated from Austrian patients).

Surprisingly, it turned out that these antibodies recognize and bind to two different antigenic determinants of the glycoprotein gp160 of HIV-1.

Moreover, It appears that the binding target of these antibodies is extraordinarily unique. In a comparative test involving a mixture of 41 different HIV-1 binding antibodies supplied by laboratories from different companies and research institutes, it was shown that no one of the other antibodies present in the mixture competed with an antibody of the above-identified group, for instance with the human monoclonal antibody from cell line CL2, for binding to the targeted antigenic fragments of gp120/gp160 corresponding to amino acid sequences 79 to 184 and 326 to 400 of processed gp120 of HIV-1 isolate BH10.

Also, investigations of blood serum and blood plasma of HIV-1 infected patients revealed that antibodies of the CL2 type were not present in the samples tested so far. This finding again emphasizes the uniqueness of these HIV-1 neutralizing human monoclonal antibodies and simultaneously indicates that there might exist an extraordinary potential to combat HIV-1 infection, by using these antibodies in a suitable form for the prophylactic and/or therapeutic treatment of human individuals.

Another object of the present invention relates to antibodies of the CL2 type which have been found to bind to the above-mentioned antigenic determinants of gp120/gp160 only if the determinants are present in a glycosylated form; they do not bind to these antigenic glycopeptide fragments when the fragments are deglycosylated, e.g., by the action of Peptide-N-Glycosidase F (EC 3.2.2.18; hereinafter referred to as "PN Gase F").

Still another object of the present invention encompasses human monoclonal antibodies of the CL2 type which are further characterized in that they also specifically bind to a fragment of gp120 produced in the SF9 insect cell/Baculovirus expression system in the absence of tunicamycin, while they do not bind to gp120 fragments expressed in the presence of tunicamycin. Tunicamycin is known for its inhibitory activity toward the glycosylating action of glycosyl transferase in glycoprotein biosynthesis.

Among the antibodies of the CL2 type as disclosed herein, there are also types which inhibit the infection of human lymphocytes by primary HIV-1 isolates such as the ones listed herein, as could successfully be demonstrated by the inventors in in vitro experiments.

The present Invention also relates to antibodies of the CL2 type which possess one or more of the above-mentioned properties and which can further be characterized by their special interaction with the anti-idiotypic monoclonal antibodies of hybridoma cell lines CL5 and CL6. While they can be bound by one and/or the other of the two anti-idiotypic antibodies CL5 and CL6, at least part of them is bound by anti-idiotypic human produced by CL6 in a way that results in a specific blockade of the capability of the antibody to Inhibit the infection of human lymphocytes by primary HIV-1 isolates.

A further object of the present invention comprises antibodies of the CL2 type which show at least one of the above-mentioned features or properties and which—in addition—have been proved to compete for binding to the antigenic determinants of gp120/160 with the antibody produced by hybridoma cell line CL2. The antibodies of this category are therefore—at least functionally—very closely related with the antibody released by CL2, and can be regarded as functional equivalents to it.

Another object of the present invention is directed to the most beneficial human monoclonal antibody produced by hybridoma cell line CL2. This antibody can be used, e.g., for passive immunization of HIV-1 infected individuals, but may even be more useful as a biochemical tool for developing vaccines applicable in the prevention and/or therapy of HIV-1 infections in vivo.

An attractive object of the present invention comprises the use of recombinant CHO cells for the production of the antibodies of the CL2 type. After successful identification of the antigenic determinants recognized and bound by these antibodies, the inventors also succeeded in transforming the respective genetic information into CHO cells, resulting In a stable cell line CL3, which synthesizes the CL2 type antibodies in a more efficient manner than the hybridoma cell line CL2 itself, In another embodiment, anti-idiotypic antibodies are disclosed which can specifically bind to idiotypic antibodies of the CL2 type and/or which can interact with at least some of them in a fashion that eliminates their anti-HIV protective capability, i.e., bars them from inhibiting the infection of human lymphocytes by primary HIV-1 isolates. Such anti-idiotypic antibodies are therefore expected to be conformationally related to the HIV-1 viruses in that they probably contain similar or even identical antigenic fragments of a viral glycoprotein, e.g., of gp160.

The antibodies of the next embodiment seem to be very interesting because they are of an anti-idiotypic type and combine the features of the anti-idiotypic antibodies of the previous embodiment with their ability to induce—upon administration to a mammal, e.g., a human or animal individual—the production and release of anti-HIV-1 antibodies. Optionally, the induced antibodies are of a nature such that they compete for binding to the above specified antigenic determinants of gp120/160 with at least one antibody of the CL2 type as hereinbefore described in any one of the respective embodiments. A special representative of this group of anti-idiotypic antibodies is the one produced by hybridoma cell line CL6.

While the anti-idiotypic antibodies of the preceding embodiment may be used for active immunization of test animals or HIV-1 endangered and preferably not yet infected persons, the antibodies induced upon such active immunization may serve as components of a vaccine for passive immunization or as subjects of investigation to design and/or synthetically or genetically prepare such antibodies. Optionally, these (idiotypic) antibodies are functional equivalents to the CL2 type antibodies i.e., they compete with the CL2 type antibodies for binding to the above specified antigenic determinants of gp120/gp160.

In a further—most exciting—embodiment of the invention, the human monoclonal antibodies exhibit strong HIV-1 neutralizing activity and bind to the smaller subunit of gp160, hereinafter referred to as gp41/gp160. Preclinical studies have proved that they are able to significantly reduce—upon intravenous administration to a human HIV-1 infected individual—the level of circulating HIV-1 in the blood serum and/or blood plasma of said individual (see Example 8 and FIG. 6).

Moreover, at least part of these antibodies may be further characterized in that they also compete with an idiotypic antibody produced by hybridoma cell line CL1 for binding to the gp41/gp 66 antigenic determinant. Finally, the antibody produced by said cell line CL1 itself can be regarded as an important member of this group of HIV-1 level reducing antibodies.

Similarly to the situation with the CHO cell line CL3 producing CL2 type antibodies, the inventors also succeeded in cloning a recombinant CHO cell line CL4 producing antibodies which compete with the antibody of CL1 for binding to the gp41/gp160 antigenic determinant and hence may be regarded as more or less close equivalents to the CL1 antibody. Such recombinant CHO cell lines are easier to grow and more efficiently employed in the manufacture of the respective antibodies.

Various in vitro experiments have proved that the CL2 type antibodies as well as the CL1 type antibodies are able to neutralize a variety of different laboratory and primary HIV-1 isolates including a number of escape mutants, which usually develop upon individual application of any one of these antibodies. It could further be shown that both antibody types are cross-reactive, i.e., they interact synergistically in that each of them is able to capture the escaped HIV-1 mutants of the other antibody. Combined in a mixture, they are therefore a powerful tool to combat HIV-1 infections and AIDS. It is one of the objects of the present invention to provide for a mixture of at least one antibody of the CL1 type and at least one antibody of the CL2 type.

The present invention also relates to a cell line producing any one of the antibodies described above, and In particular, to the cell lines CL1 through CL6 identified by their accession numbers as described below. Viable samples of the hybridoma cell lines CL1 to CL6 producing the monoclonal antibodies herein described were deposited at the European Collection of Animal Cell Cultures (ECACC) at the Public Health Laboratory Service (PHLS), Centre for Applied Microbiology and Research, Porton Down, Salisbury SP4 OJG, United Kingdom. They are identified by their accession numbers:

CL1—Accession No. 90091704 (deposited on Sep. 17, 1990);

CL2—Accession No. 93091517 (deposited on Sep. 15, 1993);

CL3—Accession No. 96032235 (deposited on Mar. 22, 1995);

CL4—Accession No. 95032236 (deposited on Mar. 22, 1996);

CL5—Accession No. 95032240 (deposited on Mar. 22, 1995); and

CL6—Accession No. 95032241 (deposited on Mar. 22, 1995).

The corresponding monoclonal antibodies produced by these cell lines are hereinafter termed MAb CL1, MAb CL2 through MAb CL6, when used In the abbreviated form.

In a further embodiment of the present invention, peptide fragments are provided which contain at least one of the antigenic determinants of gp41/gp160 and gp120/gp160 as herein described. It is desired that these peptide fragments are of a nature such that they are able to induce an immune response against HIV-1 infection, optionally the production and/or release of HIV-1 neutralizing antibodies, after administration to mammals, e.g., to an animal or a human individual.

In another embodiment, these peptide fragments may be linked to a suitable carrier in order to improve the efficacy of antigen presentation to the immune system. Such carriers may be, for instance, organic polymers including proteins, but any other appropriate and physiologically acceptable carrier may also be used, including tetanus toxoid, cholera toxin, keyhole limpet hemocyan, glutathione S-transferase and all viruses that can be modified by recombinant DNA technology such as, e.g. Rhino-, Polio-, Vaccinia-, or Influenzavirus, etc. It may be advantageous in many cases to have the peptide fragments linked to a modified, i.e., attenuated and/or recombinant virus such as modified influenza virus or modified hepatitis B virus or to parts of a virus, e.g., to a viral glycoprotein such as, e.g., hemagglutinin of influenza virus or surface antigen of hepatitis B virus, in order to increase the Immunological response against HIV-1 viruses and/or infected cells.

It is also an important object of the present invention to provide for the manufacture of a reliable vaccine to protect people from HIV-1 infection and/or to treat patients with already manifest HIV-1 infections in the course of a therapy. Vaccines based on at least one of the idiotypic antibodies of the CL2 and CL1 groups can be employed for active immunization in the prophylaxis and therapy of higher animals including man. Convincing evidence are provided below for the reduction of the HIV-1 level in the plasma and serum of a seropositive patient in the course of a therapeutic treatment in a preclinical study (cf. Example 8 and FIG. 6). Also, the preventive potency of the idiotypic antibodies of cell line CL1 was demonstrated in an impressive SCID-mouse trial as well as in a chimpanzee experiment. Neither the antibody-treated mice nor the chimpanzees developed HIV-1 infection upon challenge with live HIV-1 virus, while the animals in the untreated control groups became infected.

The use of at least one anti-idiotypic antibody as hereinbefore described for the manufacture of a vaccine for active immunization can help to successfully combat HIV-1 infection. The anti-idiotypic antibodies—as well as the drugs and vaccines derived therefrom—may primarily be used for the preventive treatment of HIV-1 endangered people and are optimally applied prior to coming into contact with HIV-1 virus. Due to their unique paratope characteristics they may also be administered to already infected patients in order to stimulate the immune system to release the corresponding—and possibly even more powerful—HIV-1 neutralizing antibodies. They may be either directly administered to a person or in combination with at least one suitable carrier and/or additive as usual in the art, and/or along with additional drugs such as, for instance, nucleoside analogues (e.g. AZT, ddl), cytokines (e.g. interleukins), HIV-protease inhibitors, antibiotics, etc. The anti-idiotypic antibodies may, however, also serve as "model templates" for the design and construction of, e.g., fusion proteins carrying their respective antigenic determinant(s) (paratopes). it might be preferable in many cases to combine an individual antibody or a mixture of at least two different antibodies with an immunoserum and/or an antibiotic, in order to further improve the benefit of an antibody vaccine manufactured accordingly.

In other cases it might be advantageous to use at least one of the herein, specified antigenic peptide fragments of gp41/gp160 and gp120/gp180 to substitute the anti-idiotypic antibodies in the corresponding vaccines and drugs. Therefore the present invention also relates to said peptide fragments and to the use thereof for the manufacture of drugs and/or vaccines applicable in the prophylactic and/or therapeutic treatment of HIV-1 endangered or HIV-1 infected people. The fragments are preferably applied as fusion proteins, wherein they are linked to a suitable carrier which might be a recombinant or attenuated virus or a part of a virus such as, e.g., the hemagglutinin of influenza virus or the surface antigen of hepatitis B virus, or another suitable carrier including other viral surface proteins, e.g., surface proteins of Rhinovirus, Poliovirus, Sindbis virus, Coxsackievirus, etc., for efficient presentation of the antigenic site(s) to the immune system. In some cases, the antigenic fragments might, however, also be purely, i.e., without attachment to a carrier, applied in an analytical or therapeutical program. It is of considerable benefit that the fragments can be used for the prevention and/or treatment of HIV-1 infections in human individuals such as persons belonging to one of the high-risk groups of HIV-1 endangered people including medical and scientific staff dealing with HIV-1 viruses and /or infected individuals.

The idiotypic antibodies referred to herein may further be used for the detection and/or determination of HIV-1 infected cells and/or HIV-1 viruses, either as individual antibodies or as an antibody cocktail. Similarly, one or more of the anti-idiotypic antibodies and/or the above-specified peptide fragments can successfully be applied to detect and/or determine anti-HIV-1 antibodies binding to the viruses or to HIV-1 infected cells. Both the idiotypic and anti-idiotypic antibodies of the present invention may therefore be prepared and arranged for an analytical testing procedure and/or for a commercially utilizable test kit.

Finally, it is also an object of the present invention to provide a method of treating HIV-1 infected persons in need of ouch treatment, and to provide for a method of preventing people from becoming HIV-1 infected. Patients with manifest HIV-1 infections may be therapeutically treated with a vaccine comprising at least one of the idiotypic antibodies of the CL2 and the CL1 type, preferably a mixture thereof. However, in some cases it might be preferable to administer at least one of the anti-idiotypic antibodies and/or antigenic peptide fragments in order to induce additional—possibly even more powerful—antibodies to neutralize the viruses and to reduce the HIV-1 levels in the blood of infected patients.

The vaccine based on antibodies and/or antigenic peptide fragments may further comprise suitable, i.e., physiologically acceptable, carriers—preferably for the preparation of injection solutions—and further additives as usually applied in the art (stabilizers, preservatives, etc.), as well as additional drugs. The patients may be administered a dose of approximately 1 to 10 $\mu$g/kg body weight, preferably by intravenous injection once a day. For less threatening cases or long-lasting therapies the dose may be lowered to 0.5 to 5 $\mu$g/kg body Weight per day. The treatment may be repeated in periodic intervals, e.g., two to three times per day, or in daily or weekly intervals, depending on the status of the infection.

Vaccines according to the present invention may comprise any one of the idiotypic or anti-idiotypic antibodies or any one of the peptide fragments disclosed herein, either alone or in combination with suitable carriers and/or linked to carrier molecules. In some cases, e.g., where HIV-1 infection is acute and/or has already considerably progressed, it might be preferable to apply a mixture of idiotypic antibodies, while in other cases it might be more beneficial to apply a mixture of anti-idiotypic antibodies and/or—preferably carrier-linked—gp160 peptide fragments. It is recommended to apply a dose of 0.5 to 10 $\mu$g/kg body weight of antibody or carrier-linked gp160 peptide fragments, administered once to three times a day and possibly repeated in periodic intervals, e.g., weekly, monthly or yearly intervals, depending on the status of HIV-1 infection or the estimated threat of an individual of getting HIV infected.

In order that the invention described herein may be more fully understood, the following examples are set forth. It should be understood that these examples are for illustrative purposes only and are not to be construed as limiting this invention in any respect.

EXAMPLE 1

(FIG. 1): Reactivity of GST/HIV-gp120 fusion proteins with antibodies from cell CL2

Figure 1:
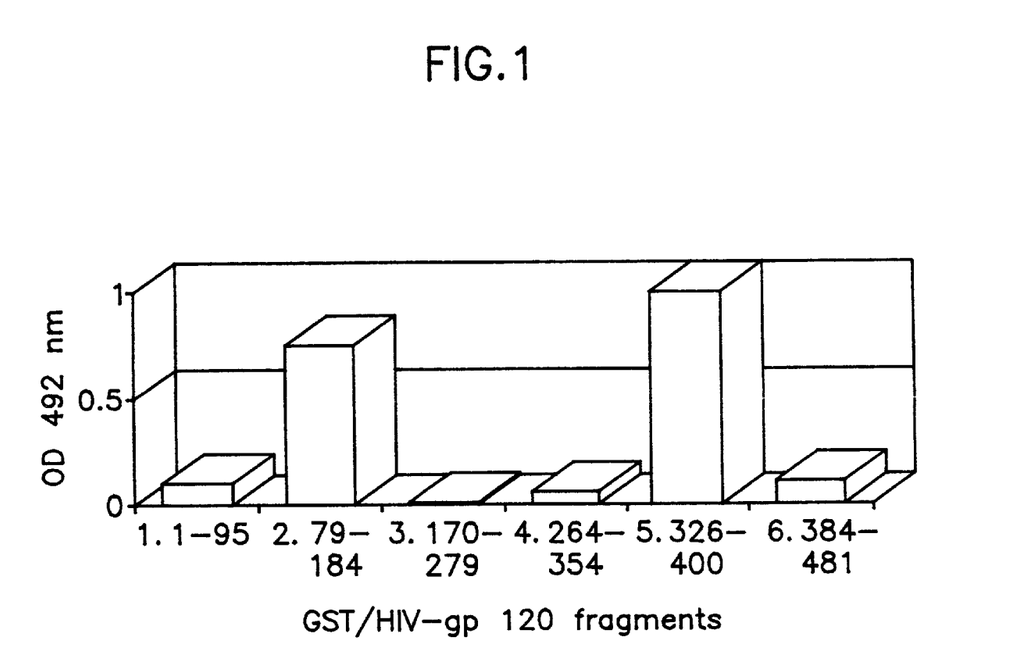
FIG. 1 shows the specific binding of a human monoclonal antibody released by hybridoma cell line CL2 with two distinct fragments of glycoprotein subunit gp120 of HIV-1; the numerals indicate the position numbers of the amino acids of the gp120 fragments as herein described.

The binding characteristics of the human monoclonal antibody produced by CL2 (referred to hereinafter as MAb CL2) to the HIV-1 envelope glycoprotein gp120:

Overlapping gp120 fragments were fused to Glutathione S-transferase (GST) and expressed using the insect cell/baculovirus system. Cell lysates of SF9 cells infected with recombinant baculovirus clones expressing different GST-gp120 fragments were first tested for their production level of GST. Lysates of GST-gp120 fusion proteins were then analysed in order to determine the binding affinity of MAb CL2. OD values of MAb CL2 given in the figure correspond to different rgp120 fragments. Microtiter plates were pre-coated with 2 μg/ml glutathione, cell lysates were added and incubated for 1 hour followed by an incubation step of 1 hour with 1 μg/ml MAb CL2 and detection with horseradish peroxidase conjugated anti-human IgG. The optical densities of the cell lysates corresponding to an equal amount of the GST fusion protein are shown.

In FIG. 1, GST-fusion-protein containing fragment 1 corresponds to amino acids 1–95 of processed gp120 of the BH10 isolate of HIV-1, fragment 2 corresponds to amino acids 79–184 of gp120, fragment 3 to amino acids 170–279, fragment 4 to amino acids 264–354, fragment 5 to amino acids 326–400 and fragment 6 to amino acids 384–481. FIG. 1 demonstrates that MAb CL2 binds to two different fragments of gp120, namely to fragment 2 (amino acids 79–184) and to fragment 5 (amino acids 326–400).

EXAMPLE 2

Figure 2:
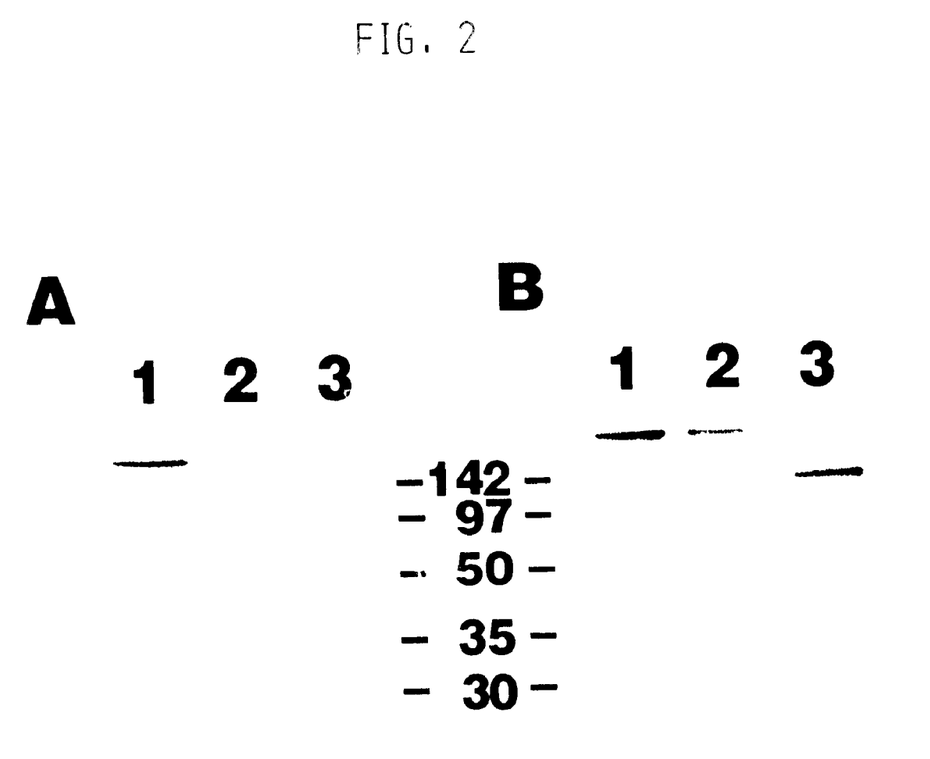

(FIG. 2): Antibody binding to deglycosylated gp160$_{HIV\ MN}$

For N-deglycosylation protein samples (500 ng recombinant gp160 of HIV-1 isolate MN) were boiled 10 min. in denaturation buffer (0.5% SDS. 1% β-Mercaptoethanol). Then ⅒ volume each of 10× enzyme reaction buffer and 10% NP-40 (polyglycol ether surfactant; Tergitol ®) were added. This reaction mixture was incubated with 2000 U of PNGaseF (Boehringer Mannheim) for 12 hours at 37° C. Polyacrylamide gel electrophoresis was performed on gels in 10–20% Tris/Glycin. After protein blotting identical membranes were incubated with 5 μg/ml MAb CL2 (panel A), and 5 μg/ml MAb CL1 (panel B) as control.

In FIG. 2 lanes 1 to 3 contain the following.

lanes 1: untreated gp160$_{HIV\ MN}$;

lanes 2: gp160$_{HIV\ MN}$ conditioned for PNGaseF treatment without enzyme;

lanes 3: gp160$_{HIV\ MN}$ PNGaseF treated;

molecular weight markers are indicated in kDa.

It can be seen in FIG. 2 that MAb CL2 does not bind to gp160 after the deglycosylating action of PNGaseF (panel A, lane 3), while MAb CL1 binds to the PNGaseF treated gp160 (panel B, lane 3).

EXAMPLE 3

(FIG. 3): Reactivity of recombinant GST/HIVgp120 fusion protein with MAb CL2 and anti-GST antiserum in the presence and absence of tunicamycin (TM)

Figure 3:
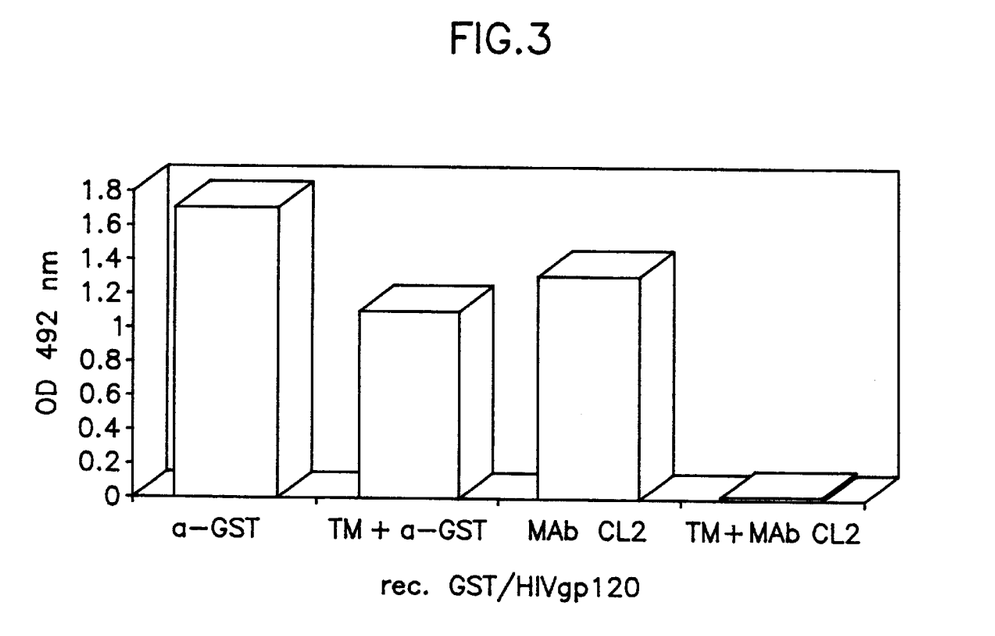
FIG. 3 shows the reactivity of anti-GST antiserum and a CL2 antibody with a recombinant gp120 in the presence and absence of tunicamycin; while a-GST binds to rec.GST/HIVgp120 in the presence of tunicamycin (at a reduced level) the CL2 antibody does not (bar 4)

SF9 insect-cells were infected with either wildtype baculovirus or GST-gp120 expressing recombinant baculovirus. 5 hours after infection, tunicamycin was added to a final concentration of 5 μg/ml. Cells were harvested after 48 hours and lysed. Anti-GST reactivity and MAb CL2 reactivity were tested by ELISA. Baculovirus infected cell-lysates (obtained from 1×10⁷ cells/ml) were transferred to microtiter plates, which were precoated with 2 μg/ml glutathione and incubated for 1.5 hours GST-fusion protein or gp120 was detected by GST-antiserum (diluted 1:2000) or MAb 2G12 (1.5 μg/ml), respectively, and horseradish peroxidase conjugated anti-mouse/anti-human IgG. The absorbance was determined at 492 nm.

As can be seen in FIG. 3 MAb CL2 does not bind to the gp120 fusion protein in the precence of tunicamycin, whereas anti-GST does, although at a decreased level.

EXAMPLE 4

Neutralization capacity of MAb CL2 for primary HIV-1 isolates

A PBMC (=peripheral blood mononuclear cells) based neutralization assay was performed as described by Purtscher et al. (M. Purtscher et.al., 1994. Aids Research and Human Retroviruses.10/12:1651–1658, Mary Ann Liebert, Inc., Publ., 1994) by pre-incubating virus with serial antibody dilutions for 1 h at 37° C. and subsequent infection of fresh PHA (=phytohemagglutinin) stimulated PBMC prepared from HIV-negative donor buffy-coat cells.

Neutralization capacity was estimated after 7 to 12 days by comparing the amounts of p24 antigen produced by the cells in the presence or in the absence of antibody.

TABLE 1

Summary of neutralization capacity of MAb CL2 in neutralization assays using PBMC.

| primary isolate | subtype clade | neutralizing capacity |
|---|---|---|
| 92RW009 | A | +++ |
| 92RW021 | A | +++ |
| 92UG037 | A | +++ |
| 92TH014 | B | +++ |
| 92BR030 | B | +++ |
| N70-2 | B | + |
| DJ259 | C | + |
| WYG | unknown | +++ |
| WRF | unknown | +++ |
| WRB | unknown | +++ |
| WSC | unknown | + |
| WHM | unknown | + |

Key: +++ 90% neutralization at a conc. of <1 μg/ml
++ 90% neutralization at a conc. between 1 to 50 μg/ml
+ 50% neutralization at a conc. below 50 μg/ml

EXAMPLE 5

Figure 4A:
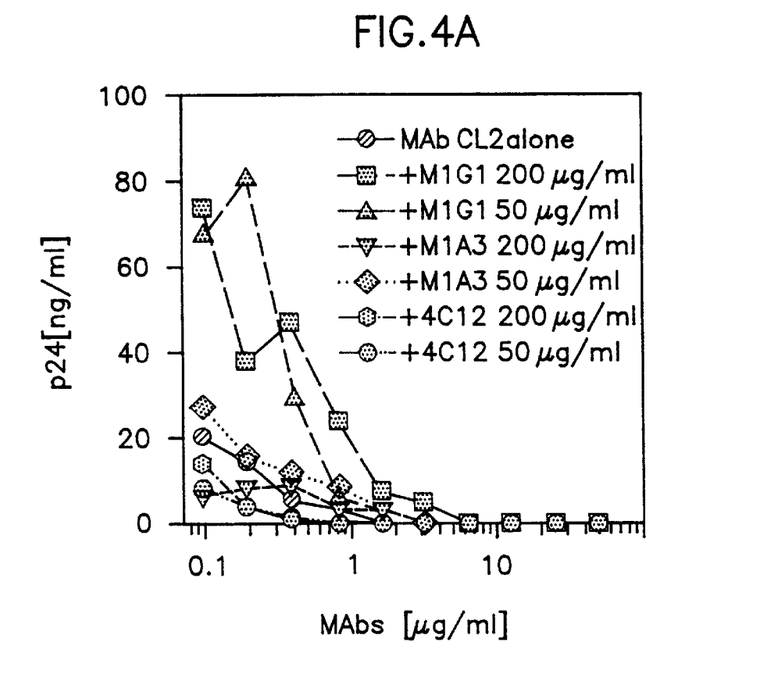
Figure 4B:
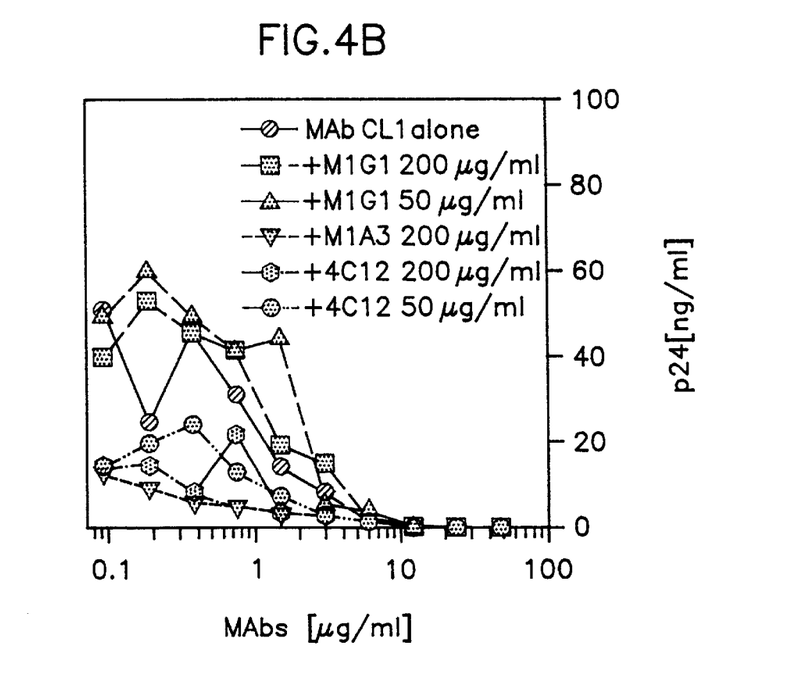

(FIG. 4): Syncytia inhibition assay/Anti-idiotype blocking

An anti-idiotype (Ab2) blocking assay was performed to determine whether the anti-idiotypic antibodies Ab2 block the neutralization capacity of MAb CL2 by binding to the neutralizing paratope of MAb CL2. The syncytia inhibition concentrations (EC$_{50}$) of MAbs CL1 and CL2 in the absence of anti-idiotypic antibodies were 2.0 and 8.8 μg/ml, respectively (the HIV-1 isolate HF was used). The addition of anti-idiotypic antibodies to MAb CL2 revealed that the antibodies M1A3 and M4C12 did not alter the neutralizing capacity, but when M1G1 (=anti-idiotypic antibody produced by CL6) was incubated with MAb CL2 a significant impairment could be observed (Table 2). The syncytia inhibiting capacity of MAb CL1, which is directed against gp41, should not be affected by the anti-idiotypic antibodies tested. No syncytia inhibition was observed with anti-idiotypic antibodies alone at a concentration of 100 μg/ml as well as with MAb 3D6, which was used as a non-neutralizing control.

TABLE 2

EC$_{50}$ of MAb CL2 and MAb CL1 in the presence of M1G1, M1A3 or M4C12

| | | anti-idiotype added (μg/ml) | | |
|---|---|---|---|---|
| MAb | alone | + M1G1 (= MAb CL6) | + M1A3 (= MAb CL5) | + M4C12 |
| | | 100 | 100 | 100 |
| MAb CL2 | 2,02 | 5,26 | 2,63 | 0,66 |
| MAb CL1 | 8,83 | 7,43 | 8,83 | 6,25 |

Anti-idiotypic antibodies were diluted to 200 μg/ml and MAbs CL2 and CL1 (as control antibody) were diluted to 10 μg/ml in RPMI 1640 medium. 50 μl of serial two-fold dilutions of MAbs CL2 and CL1 were prepared starting at 100 μg/ml in four replicates. 50 μl of anti-idiotypic antibody (200 μg/ml) were added to each well and pro-incubated for 1 h at 37° C. in the incubator. As virus inoculum the HIV-1 isolate RF was diluted to approximately $10^2-10^3$ $TCID_{50}$/ml and 50 μl of the virus suspension were added to each well. After an incubation of 1 h at 37° C., 50 μl of AA-2 cell suspension ($10^6$ cells per ml; see CHAFFEE et al. 1988, J.Exp.Med. 168:605–621) were added to each well. The cells were then cultivated during 5 days at 37° C. and 5% $CO_2$, followed by microscopical evaluation of syncytia formation. Occurrence of at least one syncytium per well was recorded as an indication of HIV-1 infection. The 50% effective concentration ($EC_{50}$) was calculated by the method of Reed and Muench (Reed, L. J. and Muench, H. 1938. A simple method of estimating fifty percent endpoints. Am.J.Hyg.27:493–497).

All wells of one dilution step were then pooled and p24 was determined quantitatively in a p24 antigen ELISA. The measured p24 values were plotted against the MAb concentration. The results thereof can be seen in FIG. 4 which displays the production of antigen p24in cultures containing MAb CL2 (graph A) and MAb CL1 (graph B) with different amounts of anti-idiotypic antibodies. Contrary to M1A3 (=MAb CL5) and 4C12, M1G1 (=MAb CL6) inhibits the neutralization activity of MAb CL2 suggesting that M1G1 at least partly mimics the paratope (of HIV-1 gp120) corresponding to the epitope of MAb CL2. The control MAb CL1 is not Inhibited by any of these antibodies. These results indicate that monoclonal antibody M1G1 is an antiidiotypic antibody to MAb CL2.

Figure 5A:
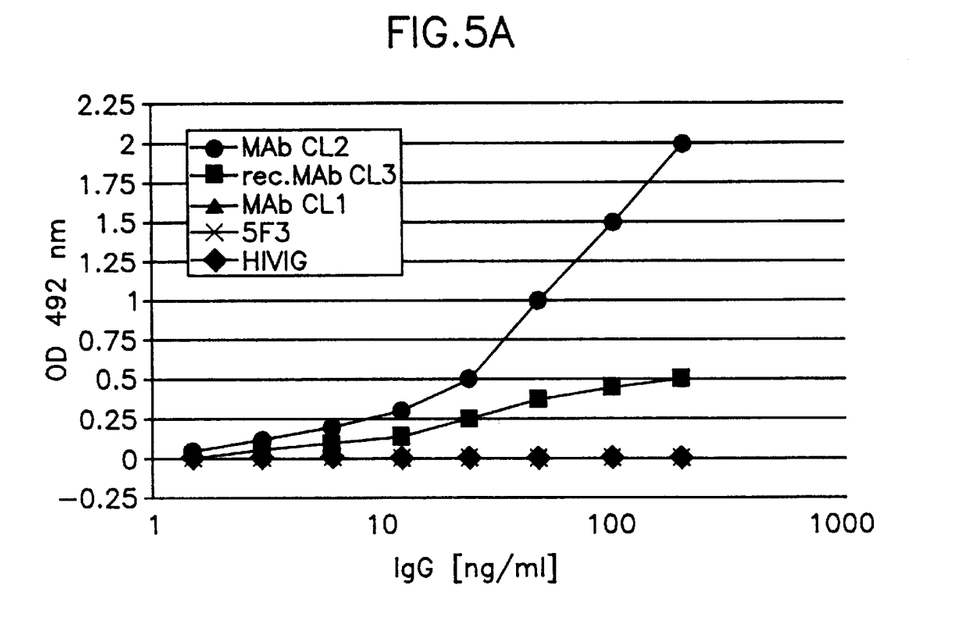
Figure 5B:
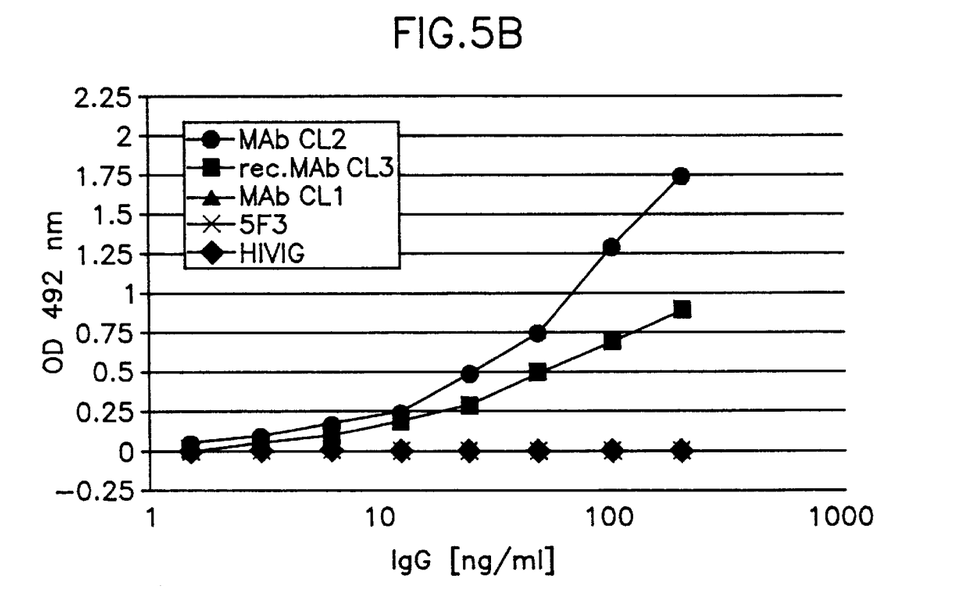

EXAMPLE 6
(FIG. 5): Reactivity of the anti-idiotypic antibodies with different anti-gp160 antibodies A panel of human anti-gp160 antibodies and pooled serum of HIV-1 positive individuals (HIVIG) were incubated on gp160-coated microtiter plates in the presence of M1G1 (=MAb CL6) and M1A3 (=MAb CL5), to prove the reactivity of the anti-idiotypes. FIG. 5, graphs A and B, show the MAb CL2-specific binding of M1G1 (graph A) and M1A3 (graph B), respectively. Both anti-idiotypic antibodies were only reactive with MAb CL2 and its recombinant double (MAb CL3) but not with other tested human antibodies (MAb CL1 and 5F3 and HIVIG are representative examples of human anti-HIV-1 antibodies), FIG. 5, graphs A and B: 96-microtiter plates were coated with 2 μg/ml gp160 (Immuno AG, Vienna). Starting dilution of the human monoclonal antibody samples began at a concentration of about 200 ng/ml and HIVIG was prediluted 1:100. Eight dilutions of the human antibodies were preformed in $2^n$ steps. M1G1 and M1A3 were used at a concentration of 1 μg/ml. The human and murine antibody dilutions were transferred to the test plate and simultaneously incubated for 1 h. Then peroxidase-conjugated goat anti-mouse IgG was applied to the plate. After 1 h of incubation staining solution was added to each well; the absorbances were read at 492 nm against 620 nm.

EXAMPLE 7
Immune selection experiments with HIV-1 molecular clone cl82.

Immune selection experiments with HIV-1 molecular clone cl82 in the presence of either MAb CL1 or MAb CL2 resulted in the generation of escape mutants at antibody concentrations lower than 6.3 μg/ml and 25 μg/ml, respectively. When both MAbs were present at the same time in the reaction mixtures virus variants evolved were only resistant to either MAb CL1 or MAb CL2. These results (Table 3) suggest that the virus cannot accumulate sufficient mutations to render itself resistant to both antibodies. Therefore, the emergence of HIV-1 escape mutants during treatment of HIV-1 infected individuals could be overcome by using a mixture of MAb CL1 and MAb CL2.

TABLE 3

| Selection conditions MAb | μg/ml | virus emerged | $EC_{50}$ > 50 μg/ml |
|---|---|---|---|
| MAb CL1 | 25 | no | |
| | 6,3 | no | |
| | 1,6 | yes | + |
| | 0,8 | yes | + |
| MAb CL2 | 25 | no | |
| | 6,3 | yes | + |
| | 1,6 | yes | + |
| | 0,8 | ND | |
| MAb CL1 + CL2 (Mixture: 50/50) | 25 | no | |
| | 6,3 | no | |
| | 1,6 | no | |
| | 0,8 | 1) | − |
| | 0,4 | 2) | − |

ND, not done
1) neutralization resistant to MAb CL2; Mixture and MAb CL1 still neutralizing;
2) neutralization resistant to MAb CL1; Mixture and MAb CL2 still neutralizing.

EXAMPLE 8
(FIG. 6): Course of p24production in cultures with serum samples from an HIV-1 infected individual before and after treatment with 3 doses of MAb CL1.

Figure 6:
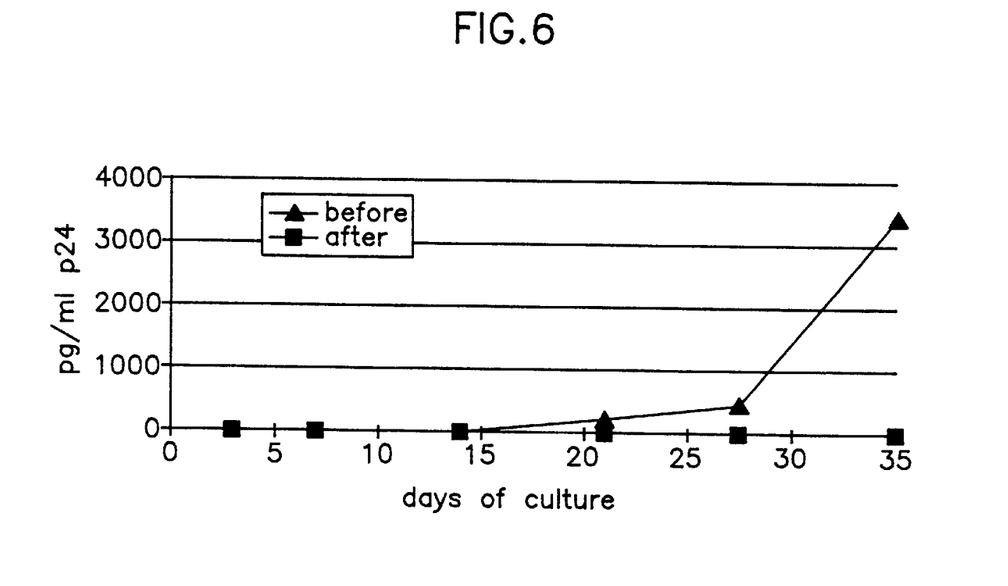

Serum was incubated with PHA-stimulated PBMC from healthy, HIV-negative blood donors. Twice a week, culture supernatant was changed 1:2 by removing half of the supernatant and substituting therefor an equal volume of fresh media. Once per week fresh PHA-stimulated PBMC were added to the culture. The culture was monitored for 5 weeks.

FIG. 6 shows the increase in syncytia formation of cultured serum samples taken from the patient before the administration of MAb CL1 (triangles) end the impressive neutralization of the patient's HIV-1 infection upon administration of MAb CL1, as displayed by the horizontal line at the zero level of p24production.

EXAMPLE 9
In vivo prevention of HIV-1 infection in a chimpanzee 4 chimpanzees have been selected for testing the in vivo neutralization in a collaboration with the Merck-research center in West Point, Pa. 19486. USA.

Prior to the in vivo test, CD4 positive primary T cells (PBMC's) were isolated from each chimpanzee to test the permissiveness of in vitro infection with the primary HIV-1 isolate, clade B. For all in vitro tests, conventional procedures as described in M. Purtscher et.al., Aids Research and Human Retroviruses, Vol. 10, Nr. 12, 1994, Mary Ann Liebert, Inc., Publ., have been used. The CD4 PBMC of all four chimpanzees were permissive to viral propagation in vitro. This was to prove that an in vivo infection should be successful.

Two of the chimpanzees were infused with the monoclonal antibody CL1 (PHLS Deposit No. 90091704). For the intravenous infusion of the antibodies 300 ml of solution containing approx. 1 mg/per mililiter stabilized in 1% human serum albumin, at pH 7 were applied per animal. Two other animals were only treated with human serum albumin.

All four chimpanzees were challenged one day after treatment with the primary HIV-1 isolate by intravenous injection of 3 chimpanzee infective doses of the virus. All four animals were routinely tested for HIV-1 infection for a period of four months.

Result: The two chimpanzees treated with antibody CL1 showed no signs of HIV-1 infection; they have been protected from infection. Both control animals, i.e., those treated only with human serum albumin, became HIV-1 positive.

EXAMPLE 10

In vivo prevention of HIV-1 infection in a SCID-mouse trial

Another experiment to demonstrate the in-vivo neutralization ability of MAb CL1 has been carried out in collaboration with Transgene, Strasbourg, France, The genes encoding the heavy and light chains of MAb CL1 have been supplied to Transgene to genetically manipulate mouse fibroblasts (3T3) using standard genetic engineering techniques. The transformed mouse fibroblasts producing MAb CL1 were propagated in vitro on GOREDEX® fibres to form cell pellets. The cell pellets were then applied under the skin of SCID mice to form organelles within these mice so as to release the MAb CL1 into the blood stream.

The SCID-mice were reconstituted using conventional procedures with the human white blood cell system in order to give an animal model suitable for infection by HIV-1.

Those SCID-mice having a level of MAb CL1 higher than 2 micrograms of antibody per ml serum were protected against a challenge with HIV-1 IIIB, whereas those having a lower level of antibody per ml in the serum showed a significant delay of infection. SCID-mice treated otherwise in an anologous way and having no MAb CL1 in their serum were all infected.

EXAMPLE 11

Detection of HIV-infection by means of HIV-1 peptide fragments and/or antiidiotypic antibodies Peptide fragments according to the present invention containing at least one of the antigenic determinants of gp41/gp160 and gp120/gp160 as herein described and/or antiidiotypic antibodies recognizing and binding to the epitope of MAb CL1 or MAb CL2 are coated onto microtiter plates by known procedures. Then, sera or plasma of HIV-1 infected patients are added to the precoated wells, whereupon anti-HIV-1 antibodies captured by the HIV-1 specific peptide fragments and/or by said antiidiotypic antibodies are detected by an anti-human IgG specific antibody conjugate (e.g. IgG-horseradish peroxidase) in an ELISA. The presence of antibodies that bind to HIV-1 specific peptide fragments indicate an infection with HIV.

EXAMPLE 12

Detection of HIV-infection by means of anti-HIV antibodies

PBMC from HIV-1 endangered or infected patients are isolated by a Ficolle® density gradient centrifugation. Cells are then incubated with at least one of the HIV-1 neutralizing antibodies MAb CL1, MAb CL2, MAb CL3 and MAb CL4 and/or with functionally equivalent antibodies obtained upon active immunization of an anmial or human individual with an antiidiotypic antibody such as MAb CL6 (M1G1) or MAb CL5 (M1A3). Incubation is carried out at standard conditions e.g., at room temperature or at 37° C. for about one hour, or at 4° C. Overnight. Bound antibody, confirming an HIV infection, is detected by a fluorochrome conjugated anti-human IgG antibody and analyzed in a fluorescence activated call scanner (FACS).

We claim:

1. An HIV-1 neutralizing human monoclonal antibody that binds to two different antigenic determinants of gp120 HIV-1 in vitro.

2. The antibody according to claim 1, wherein the antigenic determinants are fragments of gP120 corresponding amino acid sequences 79 to 184 and 326 to 400 of processed gp120 of HIV-1 isolate BH 10 (numbering according to the Swissprot database entry ENV$HIV10).

3. The antibody according to claim 1, wherein said antibody does not bind to the deglycosylated form of said antigenic determinants.

4. The antibody according to claim 1, wherein said antibody specifically binds to a fragment of gp120 produced in the SF9 insect cell/Baculovirus expression system in the absence of tunicamycin, and does not bind to gp120 expressed in the presence of tunicamycin.

5. The antibody according to claim 1, wherein said antibody inhibits the infection of human lymphocytes by primary HIV-1 isolates in vitro.

6. The antibody according to claim 5, wherein the ability of said antibody to inhibit the infection of human lymphocytes by primary HIV-1 isolates is specifically blocked by a monoclonal antibody produced by cell line CL6 ECACC Accession No.95032241.

7. The antibody according to claim 1, wherein said antibody is specifically bound by a monoclonal antibody produced by at least one of the cell lines CL5 ECACC Accession No. 95032240) and CL6 (ECACC Accession No. 9503224.

8. The antibody according to claim 1, wherein said antibody competes for binding to said antigenic determinants with an antibody produced by hybridoma cell line CL2 to ECACC Accession No. 93091517.

9. The antibody according to claim 1, wherein said antibody is produced by hybridoma cell line CL2 ECACC Accession No. 93091517.

10. The antibody according to claim 1, wherein said antibody is produced by recombinant CHO cell line CL3 ECACC Accession No. 95032235.

11. A mixture comprising an HIV-1 neutralizing human monoclonal antibody as defined in claim 1, together with at least one antibody selected from the group consisting of an antibody produced by hybridoma cell line CL1 (ECACC Accession No. 90091704);

an antibody produced by recombinant CHO cell line CL4 (ECACC Accession No. 95032236); and an antibody that competes with an antibody produced by cell line CL1 or CL4 for specific binding to gp41 of HIV-1.

12. A mixture according to claim 11, wherein said mixture prevents in vitro escape of HIV-1 mutants developing upon individual application of any one of said antibodies of the mixture.

13. A monoclonal antibody producing cell line that produces a monoclonal antibody according to claim 1.

14. The cell line according to claim 13, selected from the group consisting of cell line CL2 (ECACC Accession No. 93091517), and CL3 (ECACC Accession No. 95032235).

15. An anti-HIV-1 composition, comprising an HIV-1 neutralizing human monoclonal antibody that binds to two different antigenic determinants gp120 of HIV-1 in vitro or a mixture according to claim 11, in an amount effective for neutralization of HIV-1 in vitro, and a pharmaceutically acceptable carrier.

16. The composition according to claim 15, wherein said effective amount of said HIV-1 neutralizing monoclonal antibody or of said mixture corresponds to a dose ranging from about 0.5 to about 10 $\mu$g/kg of body weight of a patient.

17. A mixture according to claim 11, further comprising an HIV-1 neutralizing antibody which binds to two different antigenic determinants of HIV-1 and which is induced upon immunization of an animal or human individual with an antibody obtained from cell line CL5 (ECACC Accession No. 95032240) or CL6 (ECACC Accession No. 95032241).

18. An HIV-1 neutralizing antibody which binds to two different antigenic determinants of HIV-1 and which is induced upon immunization of an animal or human individual with an antibody obtained from cell line CL5 (ECACC Accession No. 95032240) or CL6 (ECACC Accession No. 95032241).

19. The composition according to claim 15, in combination with an antibiotic.

20. An antibody according to claim 18 in a mixture together with at least on antibody selected from the group consisting of an HIV-1 neutralizing human monoclonal antibody that binds to two different antigenic determinants of gp120 of HIV-1 in vitro, an antibody produced by hybridoma cell line CL1 (ECACC Accession No. 90091704), an antibody produced by recombinant CHO cell line CL4 (ECACC Accession No. 95032236), and an antibody that competes with an antibody produced by cell line CL1 or CL4 for specific binding to gp41 or HIV-1.

* * * * *